United States Patent
Brave

(10) Patent No.: US 6,371,764 B1
(45) Date of Patent: *Apr. 16, 2002

(54) DENTAL INSTRUMENT FOR PLACING OBITURATOR

(76) Inventor: Dennis Gordon Brave, 10255 Osprey Trace, W. Palm Beach, FL (US) 33412

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/691,557

(22) Filed: Oct. 18, 2000

(51) Int. Cl.[7] .................................................. A61C 3/00
(52) U.S. Cl. ...................... 433/224; 433/141; 433/147; 433/159
(58) Field of Search ................................. 433/102, 224, 433/147, 141, 157, 159

(56) References Cited

U.S. PATENT DOCUMENTS

| | | | | |
|---|---|---|---|---|
| 237,062 A | * | 1/1881 | Starr | |
| 468,746 A | * | 2/1892 | How | |
| 1,003,213 A | * | 9/1911 | Skinner | |
| 1,586,302 A | * | 5/1926 | Funk | |
| 1,818,627 A | * | 8/1931 | Kerr | |
| 3,713,221 A | * | 1/1973 | Malmin | |
| 3,903,605 A | * | 9/1975 | Malmin | |
| 4,217,098 A | * | 8/1980 | Garnier | 433/147 |
| 4,247,285 A | * | 1/1981 | Roig-Greene | 433/141 |
| 4,552,531 A | * | 11/1985 | Martin | 433/147 |
| 4,894,011 A | | 1/1990 | Johnson | |
| 4,976,617 A | * | 12/1990 | Carchidi | 433/141 |
| 5,051,093 A | * | 9/1991 | Fitzmorris | 433/224 |
| 5,098,298 A | * | 3/1992 | Johnson | 433/224 |
| 5,118,297 A | | 6/1992 | Johnson | |
| 5,275,562 A | * | 1/1994 | McSpadden | 433/224 |

OTHER PUBLICATIONS

ThermaSystem Plus Instruction Manual for use with Thermafil Plus Endodontic Obturators ©2000, Dentsply Tulsa Dental.

* cited by examiner

Primary Examiner—Ralph A. Lewis
(74) Attorney, Agent, or Firm—Molly D. McKay

(57) ABSTRACT

A dental instrument for gripping and placing an obturator within an opening in a tooth located in a patient's mouth when a root canal is being performed and the method for using the same. The instrument is provided with a handle that the dental professional grips and with one or more ends for removably holding a proximal end of an obturator.

The instrument removably secures to the proximal end of the obturator by a male-female friction fit connection between an end of the instrument and the obturator, or alternately, by arms provided on an end of the instrument that removably grasp the obturator.

4 Claims, 3 Drawing Sheets

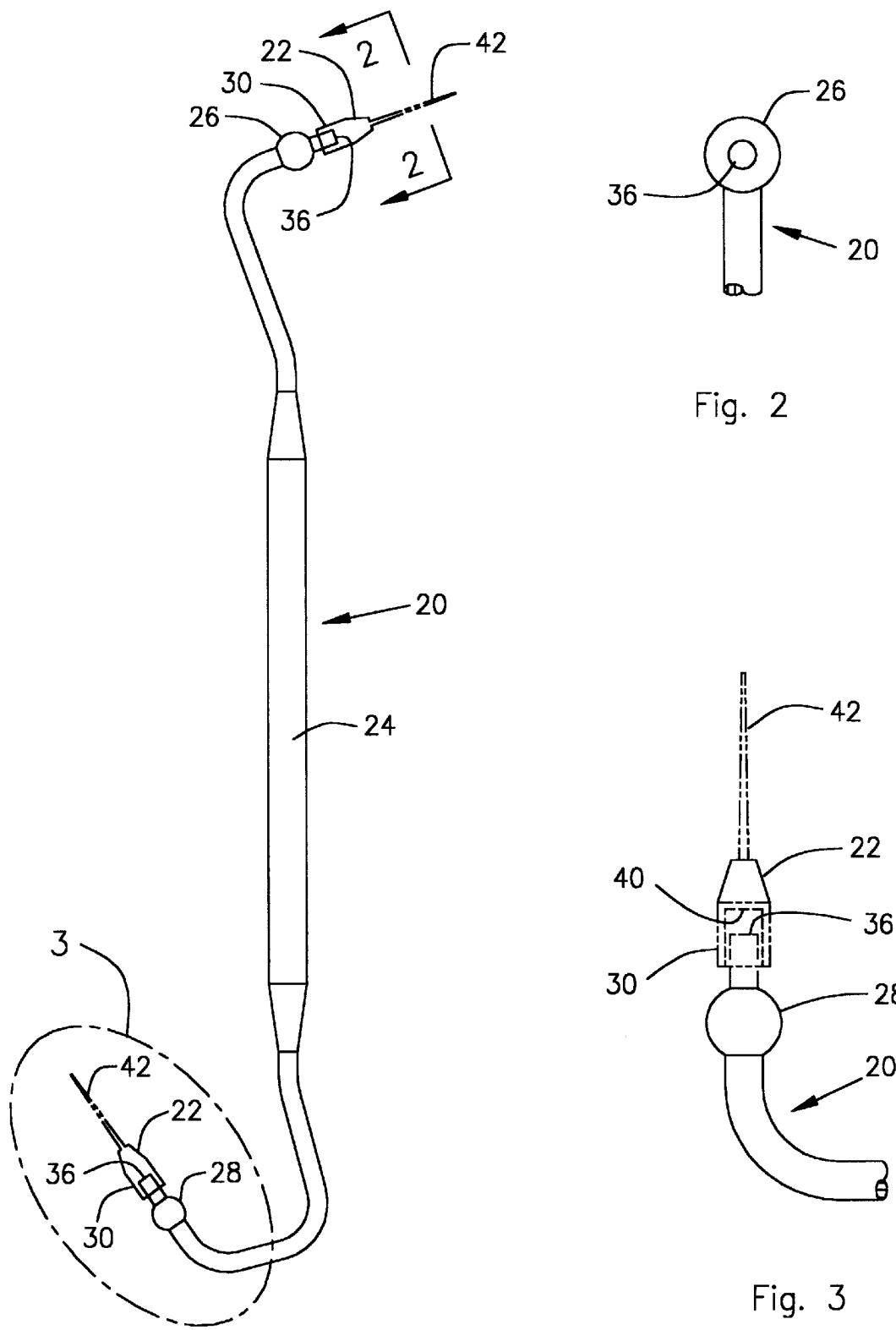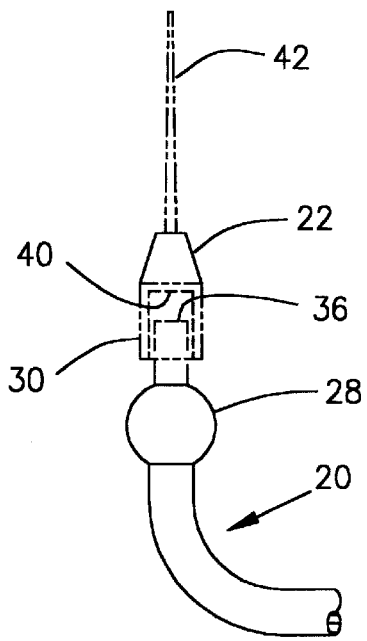
Fig. 1
Fig. 2
Fig. 3

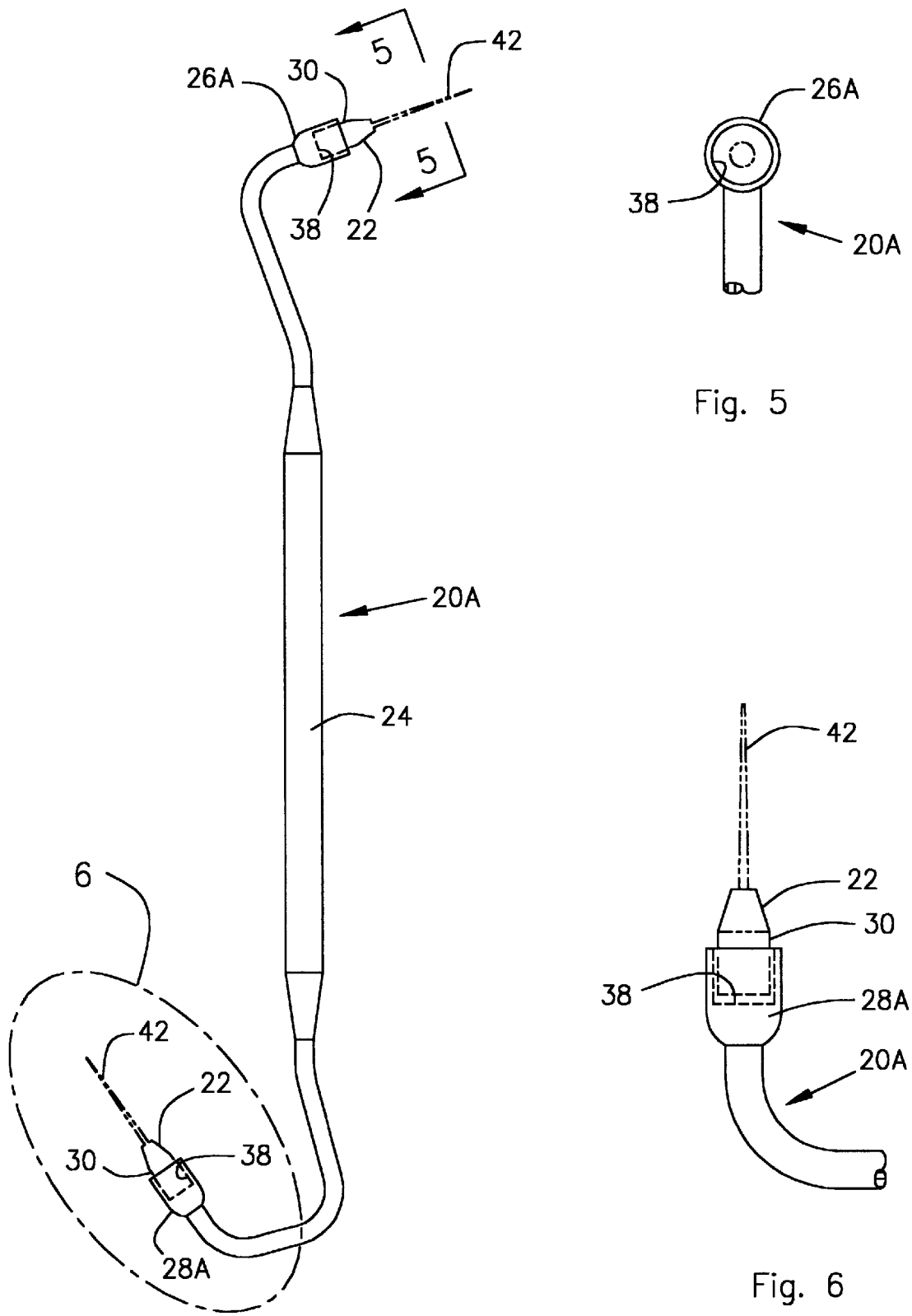

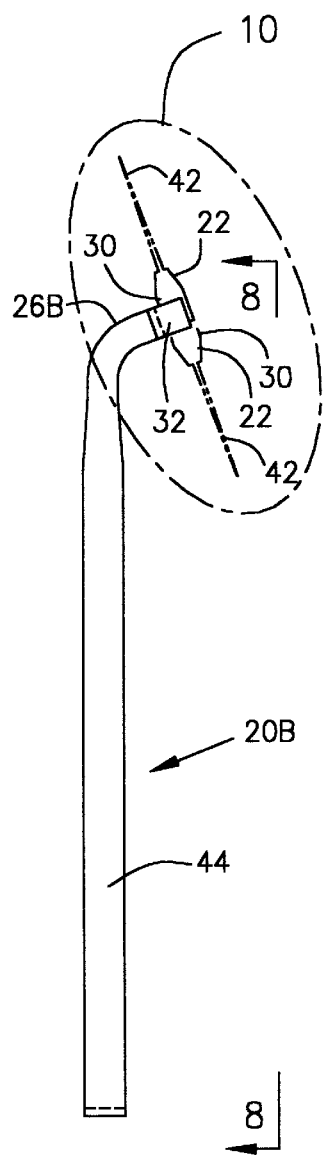
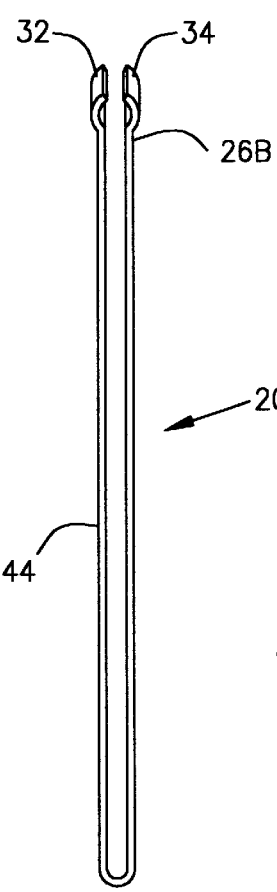
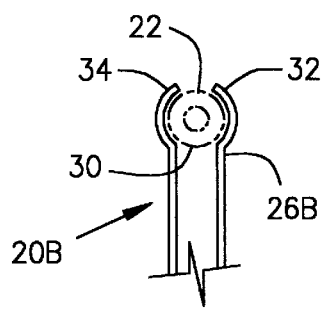
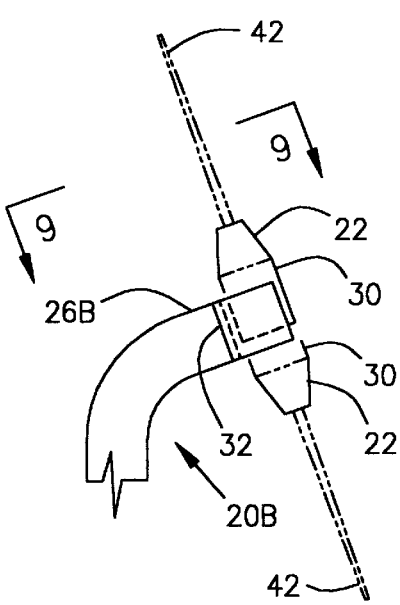
Fig. 7
Fig. 8
Fig. 9
Fig. 10

DENTAL INSTRUMENT FOR PLACING OBITURATOR

BACKGROUND OF THE INVENTION

1. Field of the Invention

The present invention relates to a dental instrument for gripping and placing an obturator within an opening in a tooth located in a patient's mouth while performing a root canal.

2. Description of the Related Art

The present invention is a dental instrument for gripping and placing an obturator within an opening in a tooth located in a patient's mouth while performing a root canal. This invention is designed to place an obturator, such as for example the type of obturator taught in U.S. Pat. No. 4,894,011. This type of obturator consists of a shaft having an enlarged proximal end for grasping the obturator and having a distal end that is generally coated with a substance such as gutta percha.

Currently there are no instruments designed to grasp an obturator while it is being placed within the patient's mouth. Without such an instrument, dental professionals currently must grasp the proximal end of the obturator with their fingers and attempt to insert the obturator into the prepared canal within the tooth undergoing the root canal procedure. Routinely the dental professional's hand obscures the operating field of vision, making insertion of the obturator difficult, particularly if patient has limited opening.

The shaft of the obturator is provided with rings that indicate the depth within the tooth that the obturator should be inserted. However, because the dental professional's hand obscures vision as the obturator is being placed, often the professional can not see the rings to determine the depth of placement within the tooth. This directly influences the prognosis of the root canal procedure.

In addition, the average dental professional will incur significant difficulty in initially attempting to grasp the proximal end of the obturator while removing it from a warming oven. If the heated obturator is mishandled or dropped, the heated gutta percha that coats the distal end of the obturator is damaged or displaced and the obturator must be discarded. Even if the professional is able to grasp the obturator and insert his hand in the patient's mouth, because his view is obscured, he often will not be successful in placing the obturator precisely within the desired opening in the tooth. Imprecise placement will occur if the heated gutta percha that coats the distal end of the obturator is stripped off of the obturator or damaged before the distal end of the obturator can be properly placed through the access opening in the tooth and thereafter into the root canal space.

The present invention addresses these problems by providing an instrument for grasping an obturator and placing it within the desired tooth opening. The instrument is designed so that the dental professional's vision is not obscured during placement, allowing for more accurate visual placement and more precise depth location of the distal end of the obturator within the tooth opening using the rings provided on the obturator shaft. Use of this instrument allows the dental professional to fill the opening in a tooth that was made to perform a root canal with a cleaner and more precise technique than when using his fingers to grip the obturator. Also, placing of the obturator using this instrument is more comfortable for the patient in that the patient is not required to open as wide as would be necessary to admit the dental professional's fingers. Because of the greater dexterity afforded to the dental professional by using this instrument, there is less chance of dropping or stripping the obturator when initially grasping it as the obturator is removed from the warming oven. Also, this instrument results in less instances of stripping the gutta percha off of the obturator during placement.

In addition, this instrument allows the dental practitioner greater vision of the operating field, easier access to the root canal space, and the potential for a better final result for his effort. Due to the reduction in waste, use of this instrument results in cost savings by reducing the number of obturators that need to be purchased by the dental professional.

SUMMARY OF THE INVENTION

The present invention is a dental instrument for gripping and placing an obturator within an opening in a tooth located in a patient's mouth when a root canal is being performed. The instrument is provided with a handle that the dental professional grips. The handle is provided with one or more ends that are each designed to be capable of removably securing to a proximal end of an obturator.

Each end of the instrument may be either friction fit to the proximal end of the obturator for precise release or may be provided with arms that firmly grasp the proximal end of the obturator. If each end of the instrument attaches to the proximal end of the obturator by friction fit, each end of the instrument may be either a female connection or a male connection. If each end of the instrument is a female connection, the female connection encases the proximal end to removably secure the proximal end of the obturator to the end of the instrument. If each end of the instrument is a male connection, the male connection inserts into a central opening provided in the proximal end of the obturator as a means of removably securing the proximal end of the obturator to the end of the instrument.

BRIEF DESCRIPTION OF THE DRAWINGS

FIG. 1 is a perspective view of a dental instrument constructed in accordance with a preferred embodiment of the present invention shown with an obturator removably attached to each of the instrument's two male connection ends.

FIG. 2 is an end view of the instrument of FIG. 1 taken along line 2—2 shown with the obturator removed.

FIG. 3 is an enlarged view of the upper end of the instrument of FIG. 1 showing details of the male connection end in removable engagement with a central opening provided in a proximal end of an obturator.

FIG. 4 is a perspective view of an alternate dental instrument constructed in accordance with a second embodiment of the present invention shown with an obturator removably attached to each of the instrument's two female connection ends.

FIG. 5 is an end view of the instrument of FIG. 4 taken along line 5—5 shown with the obturator removed.

FIG. 6 is an enlarged view of the upper end of the instrument of FIG. 4 showing details of the female connection end in removable engagement with a proximal end of an obturator.

FIG. 7 is a perspective view of a second alternate dental instrument constructed in accordance with a third embodiment of the present invention showing in outline two different orientations that obturators can be removably attached to the instrument's connection end.

FIG. 8 is a front view of the instrument of FIG. 7 taken along line 8—8 shown without an obturator being attached to the connection end.

FIG. 9 is an end view of the instrument of FIG. 10 taken along line 9—9 with an obturator shown in outline.

FIG. 10 is an enlarged view of the connection end of the instrument of FIG. 7 showing details of the two different orientations for removably engaging proximal ends of obturators with arms provided on the connection end of the instrument.

DETAILED DESCRIPTION OF THE PREFERRED EMBODIMENT

The Invention

Referring now to FIGS. 1, 2, and 3, there is illustrated a dental instrument 20 constructed in accordance with a preferred embodiment of the present invention. FIGS. 4–6 illustrate a first alternate embodiment 20A of the invention, and FIGS. 7–10 illustrate a second alternate embodiment 20B of the invention. The dental instrument 20 is designed to removably grip and place an obturator 22 within an opening in a tooth located in a patient's mouth when a root canal is being performed. The instrument 20 is provided with a handle 24 that the dental professional grips with his hand. As illustrated in FIG. 1, the instrument 20 has two ends 26 and 28 that are each designed to removably secure to a proximal end 30 of an obturator 22. It is desirable to have two ends 26 and 28 that are at different angles relative to the handle 24 so that the instrument 20 can be used to reach the varied angles of openings in teeth that are necessary when performing root canal procedures. The more curved end or back action end 28 of the two ends 26 and 28 of the instrument 20 is useful for reaching posterior teeth within a patient's mouth. However, the invention is not so limited, and the instrument 20, 20A, or 20B can be made with only one end 26 or 28 for removably securing to a proximal end 30 of an obturator 22 instead of having two ends 26 and 28.

Each end 26 and 28 of the instrument 20 friction fits to the proximal end 30 of the obturator 22, as illustrated in FIGS. 1–3. Likewise each end 26A and 28A of the alternate instrument 20A friction fits to the proximal end 30 of the obturator 22, as illustrated in FIGS. 4–6. The end 26B of the second alternate embodiment 20B is provided with arms 32 and 34 that firmly grasp the proximal end 30 of the obturator 22, as illustrated in FIGS. 7–10.

Each end 26 and 28 or 26A and 26B of the instrument 20 or 20B that attaches to the proximal end 30 of the obturator 22 by friction fit, has either a male connection 36, as illustrated in the preferred embodiment shown in FIGS. 1–3, or a female connection 38, as illustrated in the first alternate embodiment shown in FIGS. 4–6.

Referring now again to FIGS. 1–3, each end 26 and 28 of the preferred embodiment instrument 20 is a male connection 36, and each male connection 36 inserts into a central opening 40 that has previously been drilled or otherwise provided in the proximal end 30 of the obturator 22 as a means of removably securing the proximal end 30 of the obturator 22 to the end 26 or 28 of the instrument 20 by friction fit. Once the gutta percha coated distal end 42 of the obturator 22 has been properly placed in the patient's tooth and the gutta percha has been allowed to harden, then the instrument 20 can be disengaged from the proximal end 30 of the obturator 22 simply by rotating the instrument 20 to loosen the male connection 36 from the central opening 40 in the proximal end 30 of the obturator 22. The instrument 20 can then be removed from the patient's mouth and the dental professional can complete the root canal procedure.

Referring now to FIGS. 4–7, the instrument 20A is provided with a handle 24 that the dental professional grips with his hand. Each end 26A and 28A of the first alternate embodiment instrument is a female connection 38, and each female 38 connection encases the proximal end 30 an obturator 22 to removably secure the proximal end 30 of the obturator 22 to the end 26A and 28A of the instrument by friction fit. Once the gutta percha coated distal end 42 of the obturator 22 has been properly placed in the patient's tooth and the gutta percha has been allowed to harden, then the instrument 20A can be disengaged from the obturator 22. This is done by simply by rotating the instrument 20A while exerting a slight pulling away motion to loosen the female connection 38 from the proximal end 30 of the obturator 22. The instrument 20A can then be removed from the patient's mouth and the dental professional can complete the root canal procedure.

Referring now to FIGS. 8–10, the second alternate embodiment 20B has only one end 26B for grasping the proximal end 30 of the obturator 22 in order to removably secure the proximal end 30 of the obturator 22 to the end 26B of the instrument 20B. The end 26B of the second alternate embodiment 20B that grasps the obturator 22 is provided with at least two arms 32 and 34 that are curved so that they present inwardly facing concave surfaces that encircle the proximal end 30 of the obturator 22 to secure the obturator 22 between the arms 32 and 34. The alternate embodiment 20B is shaped similar to a pair of tweezers, with the arms 32 and 34 capable of moving together to grasp an obturator 22 and capable of moving away from each other in order to release the obturator 22.

In use, the arms 32 and 34 are moved toward each other in order to grasp the proximal end 30 of the obturator 22 therebetween. As illustrated in FIGS. 7 and 8, the second alternate embodiment 20B has arms 32 and 34 that are normally outwardly biased. In order to grasp the obturator 22, the dental professional grasps the handle 44 of the instrument. 20B tightly to force the normally outwardly biased arms 32 and 34 together. Once the distal end 42 of the obturator 22 has been properly placed with the opening of the patient's tooth and the gutta percha coating on the distal end of the obturator 22 has harden, then the instrument 20B can be disengaged from the proximal end 30 of the obturator 22 simply by allowing the arms 32 and 34 to move away from each other.

To release the obturator 22 from the instrument 20B, the dental professional loosens his grip on the handle 44 of the instrument 20B to allow the arms 32 and 34 to return to their normally open position, thus releasing the obturator 22. Once obturator 22 is released, the instrument 20B can then be removed from the patient's mouth and the dental professional can complete the root canal procedure.

While the invention has been described with a certain degree of particularity, it is manifest that many changes may be made in the details of construction and the arrangement of components without departing from the spirit and scope of this disclosure. It is understood that the invention is not limited to the embodiments set forth herein for the purposes of exemplification, but is to be limited only by the scope of the attached claim or claims, including the full range of equivalency to which each element thereof is entitled.

What is claimed is:

1. A dental instrument and obturator for placing the obturator in a root canal comprising:

a u-shaped articulating handle, two ends attached to the handle, each said end provided with an inwardly facing concave surface precision fit to removably engage a cylindrical proximal end of an obturator, said ends removably engaging circumpherentially a cylindrical proximal end of an obturator as a means of placing the obturator in a root canal.

2. A dental instrument and obturator according to claim 1 further comprising:

said ends provided at an angle relative to the handle so that the obturator can be grasped by the ends in two different orientations that are 180 degrees from each other.

3. A dental instrument and obturator according to claim 2 wherein the ends are provided at an angle relative to the handle such that a longitudinal axis of the handle forms an acute angle with the obturator when the obturator is grasped in one or the two different orientations and so that the handle forms an obtuse angle with the obturator when the obturator is grasped in the other orientation.

4. A method for placing an obturator while performing a root canal comprising the following steps:

a. engaging via friction fit a cylindrical proximal end of a preheated obturator with at least one end of a dental instrument so that the instrument securely holds the obturator, b. using the dental instrument to insert a distal end of the preheated obturator into a desired placement in a patient's tooth and to hold the obturator while gutta percha provided on the distal end of the obturator hardens, and c. disengaging the dental instrument from the obturator without creating any deleterious movement of the obturator.

* * * * *

UNITED STATES PATENT AND TRADEMARK OFFICE
CERTIFICATE OF CORRECTION

PATENT NO.    : 6,371,764 B1
DATED         : April 16, 2002
INVENTOR(S)   : Dennis Gordon Brave It is certified that error appears in the above-identified patent and that said Letters Patent is hereby corrected as shown below:

<u>Title page,</u>
Item [54], the title of the invention is -- DENTAL INSTRUMENT FOR PLACING OBTURATOR --.

Signed and Sealed this

Third Day of September, 2002

Attest:

Attesting Officer

JAMES E. ROGAN
*Director of the United States Patent and Trademark Office*